United States Patent [19]
Jeng et al.

[11] Patent Number: 5,372,591
[45] Date of Patent: Dec. 13, 1994

[54] SOLUTION DISPENSING DEVICE FOR INTRAVENOUS DRIP

[76] Inventors: Hwang-Roan Jeng, No. 29, Lane 332, Fu-Der Alley, Tei-Weng Hsian, Chang Hua Hsien; Jiune-Piin Yang, No. 230, Sin-Sing Rd., Si Low Chun, Yun Lin Hsien, both of Taiwan, Prov. of China

[21] Appl. No.: 154,453

[22] Filed: Nov. 19, 1993

[51] Int. Cl.⁵ ............................................. A61M 5/00
[52] U.S. Cl. ................................... 604/256; 604/127
[58] Field of Search ......................... 604/251, 127, 256

[56] References Cited

U.S. PATENT DOCUMENTS

| 2,844,147 | 7/1958 | Beacham | 604/127 |
| 3,216,419 | 11/1965 | Scislowicz | 604/127 |

FOREIGN PATENT DOCUMENTS

| 194605 | 11/1992 | Taiwan, Prov. of China . |
| 194606 | 11/1992 | Taiwan, Prov. of China . |

*Primary Examiner*—John D. Yasko
*Attorney, Agent, or Firm*—Browdy and Neimark

[57] ABSTRACT

An improved solution dispensing device for intravenous drip comprises a container of tubular construction and having at the top thereof a connecting needle piercing through the mouth of a solution bottle. The container is connected at the bottom thereof with one end of a solution transporting tube having another end that is connected with a hypodermic needle. A stopping element is disposed in the container such that the stopping element can be caused to rise or descend in accordance with the solution level. The solution transporting tube has an extension segment that is disposed in the container. The stopping element is provided with a recessed portion corresponding in location to the extension segment. As the stopping element is caused to descend so that the extension segment is enclosed by the recessed portion, a compartment is formed between the outer wall of the extension segment and the inner wall of the recessed portion. The compartment is used to contain the solution, which acts to seal off the open end of the extension segment of the solution transporting tube.

5 Claims, 6 Drawing Sheets

5,372,591

1

SOLUTION DISPENSING DEVICE FOR INTRAVENOUS DRIP

FIELD OF THE INVENTION

The present invention relates generally to an apparatus for intravenous drip, and more particularly to a solution dispensing device capable of shutting off automatically upon completion of injecting a medical solution intravenously into a patient's body.

BACKGROUND OF THE INVENTION

As shown in FIGS. 1 and 2, the intravenous drip apparatus of the prior art comprises a solution dispensing device 11 of tubular construrction. The solution dispensing device 11 is provided at the top thereof with a connecting needle 12 piercing through the mouth 14 of a drip bottle 13. Attached to the bottom end of the solution dispensing device 11 is a solution transporting tube 15, which is connected with a hypodermic needle 16 for injecting intravenously a medical solution into a person's body. The solution dispensing device 11 is provided with a space for holding the medical solution to be injected intravenously into a person's body. Disposed at the midpoint of the solution transporting tube 15 is a control switch 17 for regulating the injection speed or shutting off the solution transporting tube 15. The mouth 14 of the drip bottle 13 is provided with an air needle 18 piercing therethrough for allowing the air to enter the drip bottle 13. In operation, the drip bottle 13 is so elevated as to permit the execution of an intravenous drip. Additional medical solution can be replenished in the midst of the intravenous drip by pulling the connecting needle 12 out of the drip bottle 13 and then by piercing the connecting needle 12 into another drip bottle filled with the fresh medical solution. However, such a replenishment of solution must be done in time to prevent the blood of a person receiving the intravenous drip to flow into the hypodermic needle 16 and the solution transporting tube 15. Such an incident often results in the clogging of the hypodermic needle 16 and the solution transporting tube 15 by the coagulated blood.

With a view to overcoming the shortcoming of the intravenous drip device of the prior art described above, the Taiwanese Patent Serial Number 81208567 (FIG. 3) discloses a solution dispensing device 21 which is provided therein horizontally with a partition 22 provided centrally with a hole 23, a stopping element 24, a body 25 of columnar construction and having two semi-circular heads 26 and 27. The body 25 is disposed in the hole 23 of the partition 22 such that the two heads 26 and 27 are located respectively on upper and lower sides of the partition 22. The body 25 and the lower head 27 are provided with a slot 28. When the solution dispensing device 21 contains the solution, the stopping element 24 is caused to rise so that the lower head 27 is stopped by the partition 22. As a result, the solution is allowed to flow through the partition 22 via the slot 28. As the process of intravenous drip is completed, the stopping element 24 is caused to descend so that the hole 23 of the partition 22 is obstructed by the upper head 26, thereby preventing the air from getting into the portion under the partition 22 so as to keep the solution level at the underside of the partition 22. In other words, the solution dispensing device 21 is therefore automatically shut off.

2

Another Taiwanese Patent Serial Number 81208778 (FIG. 4) discloses a solutiion dispensing device 31 which is provided with a floatable body 32 of spherical construction and having a thin ring 33. The floatable body 32 is caused to descend to obstruct the passage of the solution to the solution transpowering tube 34 at the time when the intravenous drip is completed.

The solution dispensing devices 21 and 31 described above are defective in design in that their automatic shut-off means do not work precisely in view of the fact that the devices 21 and 31 are made of a soft plastic material and are therefore vulnerable to deformation. For example, the deformation of the stopping element 24 or the floatable body 32 can bring about a complete failure of the automatic shut-off. In addition, the partition 22 is structurally complicated and can not be therefore made easily.

SUMMARY OF THE INVENTION

It is, therefore, the primary objective of the present invention to provide an improved solution dispensing device of simple construction with means capable of shutting off the device automatically and precisely at the time when the intravenous drip is completed.

The foregoing objective of the present invention is achieved by a solution dispensing device for intravenous drip, which comprises a stopping element capable of floating in the solution. As the solution level in the solution dispensing device is lowered, the stopping element is caused to descend to shalt off the passage between the solution dispensing device and the solution transporting tube which has an extension segment of a predetermined length and extending into the solution dispensing device. The stopping element is provided with a recessed portion corresponding in location to the extension segment of the solution transporting tube. As the solution level in the dispensing device is lowered, the stopping element is caused to descend to cover the open end of the extension segment of the solution transporting tube in such a manner that a compartment is formed between the inner wall of the recessed portion of the stopping element and the outer wall of the extension segment of the solution transporting tube. The compartment has open ends lower in level than the open end of the extension segment of the solution transporting tube. As a result, the level of the solution in the dispensing device is lower than that of the open end of the extension segment. However, the compartment contains solution, which acts to shut off the open ends of the compartment so as to prevent the air from getting into the open end of the extension segment of the solution transporting tube.

DETAILED DESCRIPTION OF THE INVENTION

Figure 1:
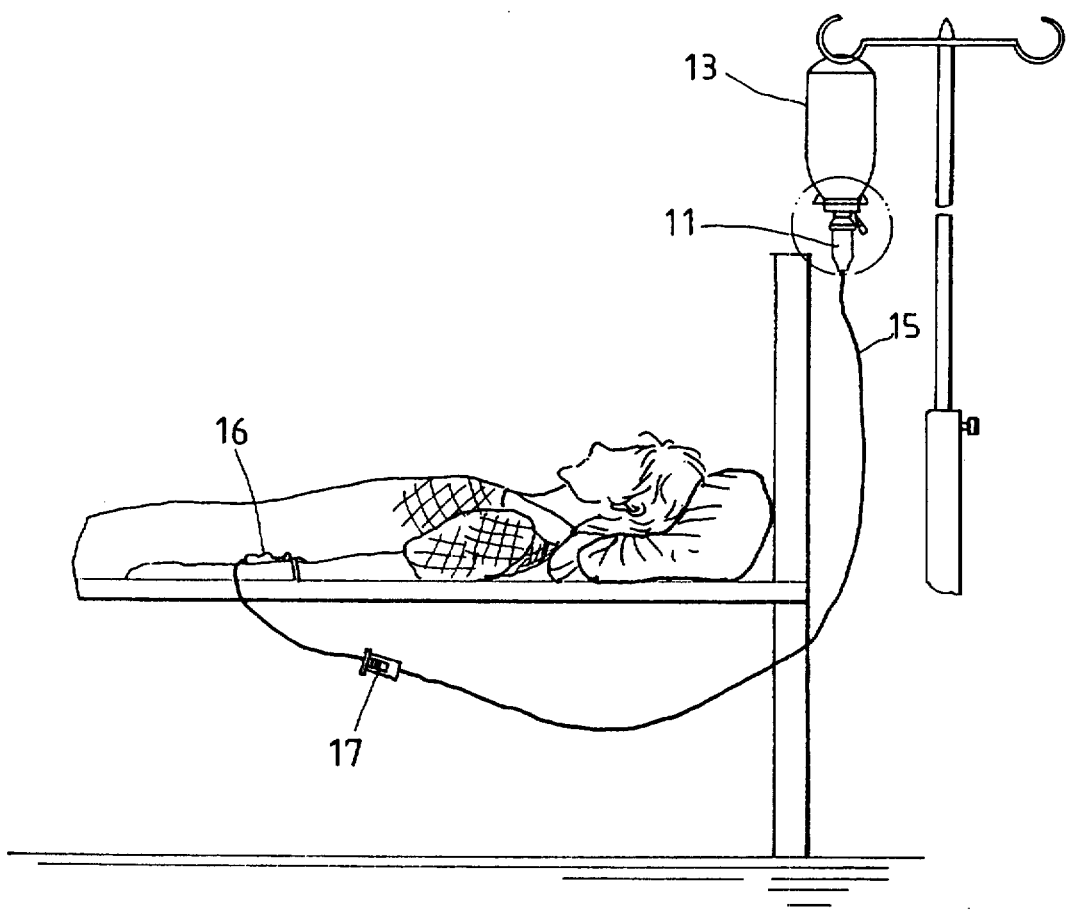
FIG. 1 is a schematic view showing the execution of an intravenous drip by means of a solution dispensing device of the prior art.
Figure 2:
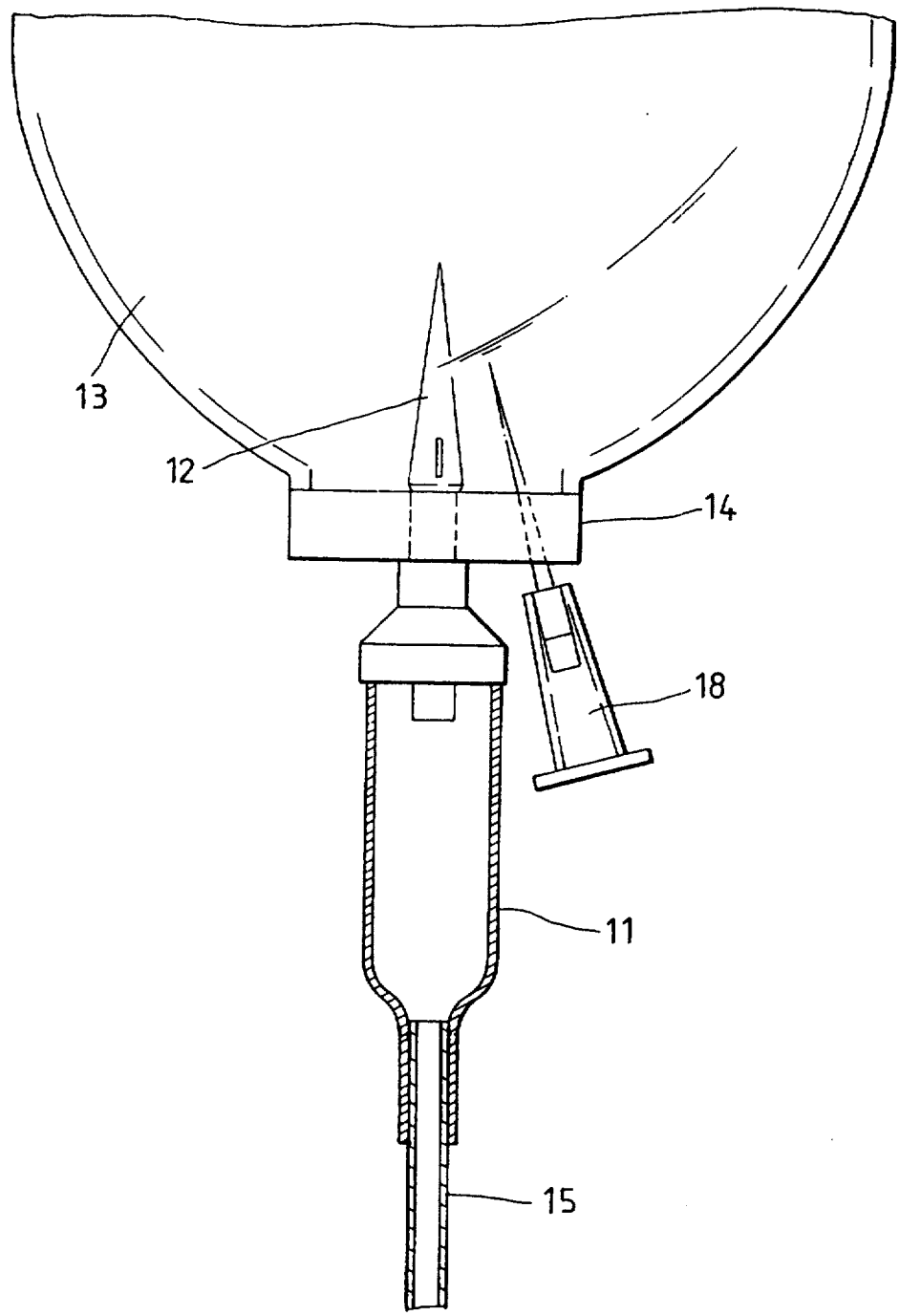
FIG. 2 is an enlarged schematic view of a circled portion as shown in FIG. 1.
Figure 3:
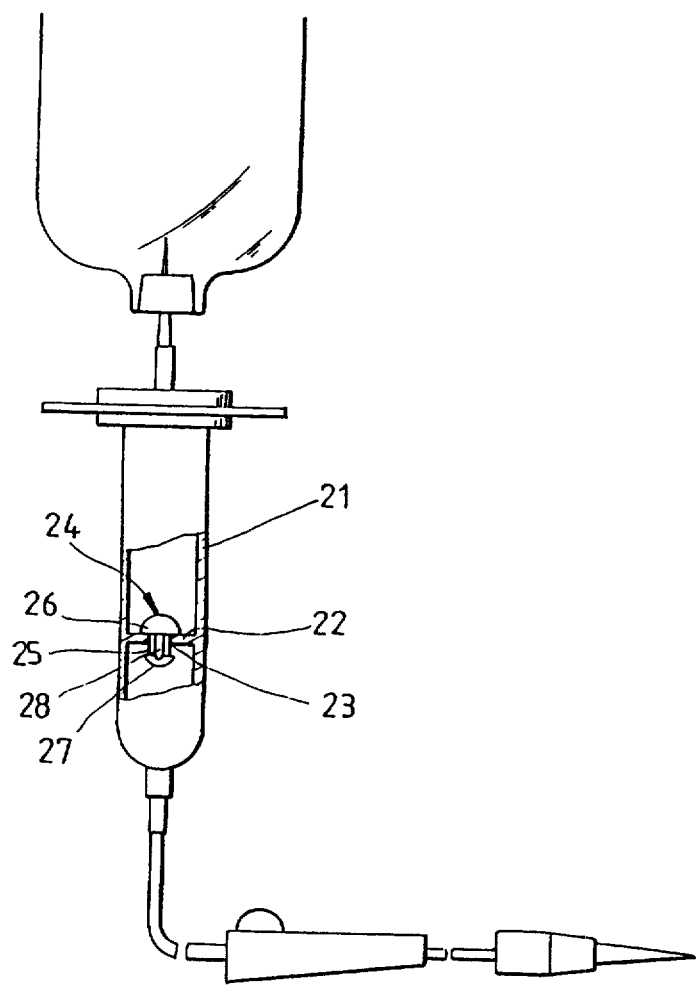
FIG. 3 is a schematic view showing the construction of a prior art solution dispensing device provided with a stopping element.
Figure 4:
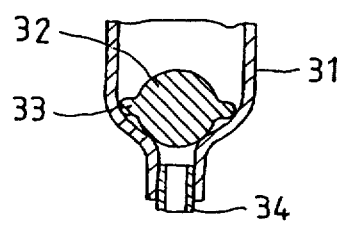
FIG. 4 is a schematic view showing the construction of another prior art solution dispensing device provided with a stopping element.
Figure 5:
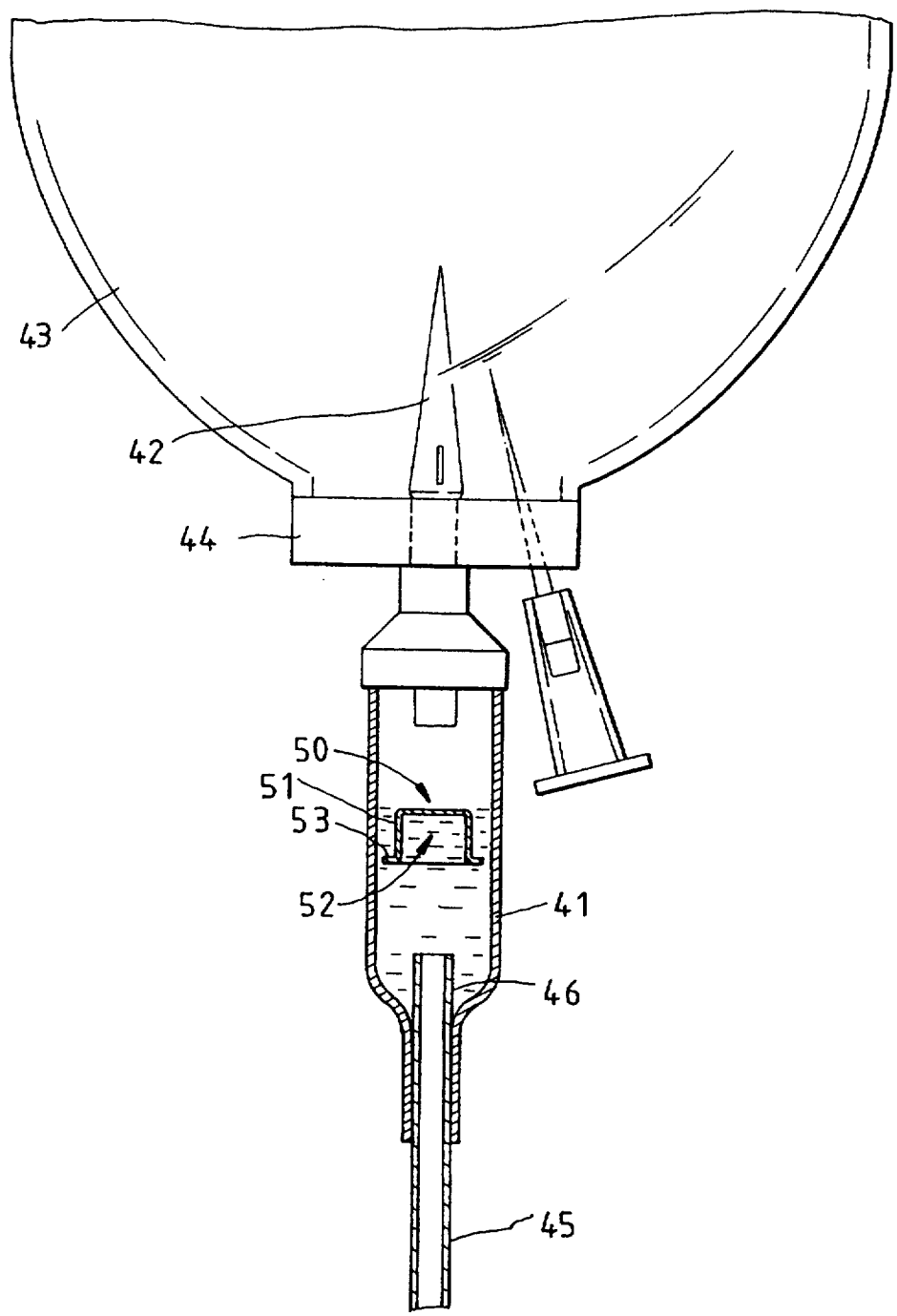
FIG. 5 shows a schematic view of a first preferred embodiment in action, according to the present invention.
Figure 6:
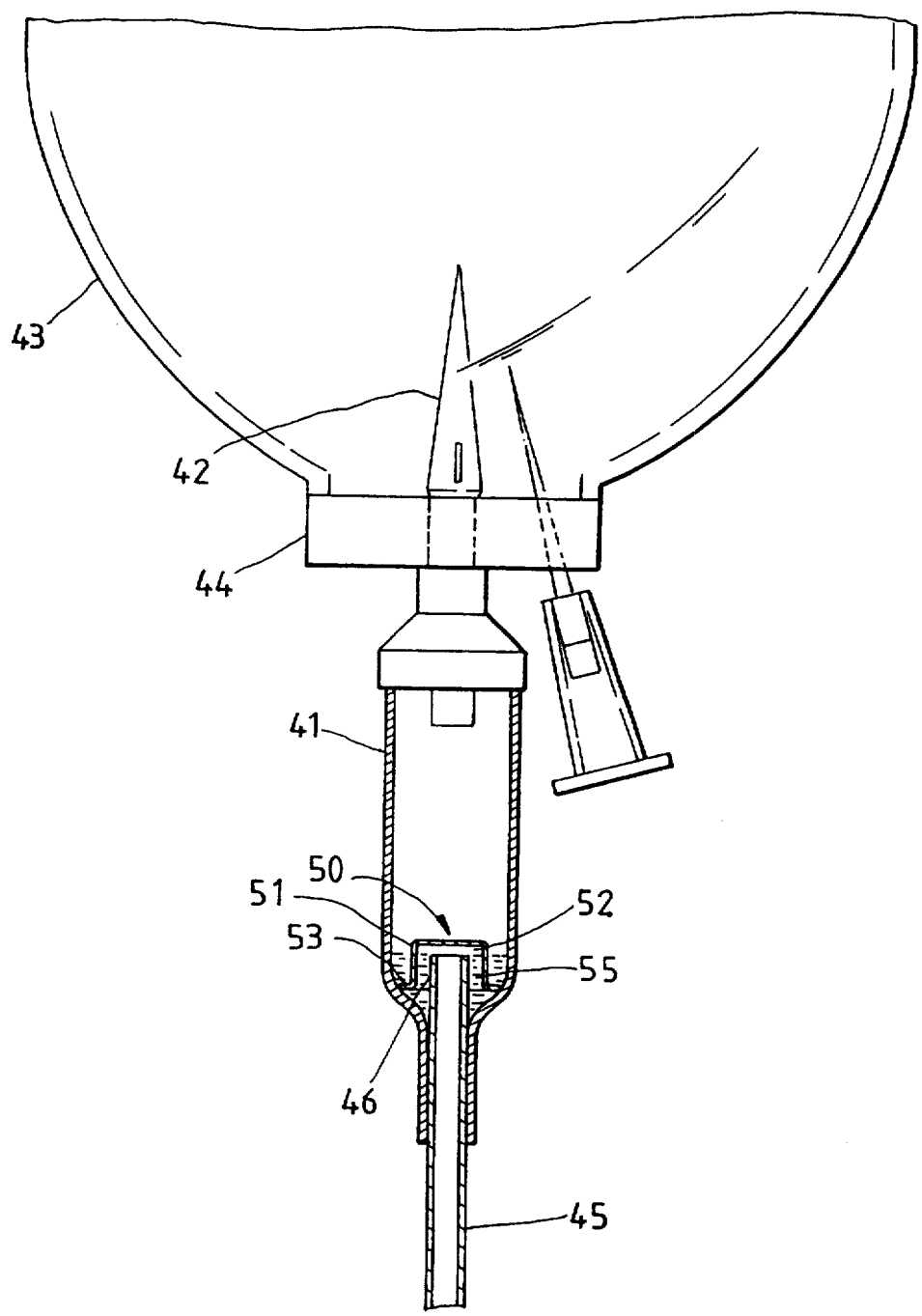
FIG. 6 shows a schematic view illustrating the automatic shut-off of the first preferred embodiment of the present invention.

Referring to FIGS. 5 and 6, a solution dispensing device 41 of the present invention is shown to comprise a connecting needle 42 piercing through the mouth 44 of a solution bottle 43. The bottom end of the solution dispensing device 41 is connected with a solution transporting tube 45 in such a manner that an extension segment 46 of the solution transporting tube 45 is disposed in the solution dispensing device 41. A stopping element 50 disposed in the solution dispensing device 41 is composed of a body 51 provided in the bottom side thereof with a recessed portion 52. The bottom side of the body 51 extends horizontally to form a collar shoulder 53 which does not make contact with the inner wall of the solution dispensing device 41. In operation, the stopping element 50 is suspended in the solution contained in the solution dispensing device 41, as shown in FIG. 5. As the intravenous drip is completed, the stopping element 50 is caused to descend along with the lowering of the solution so that the recessed portion 52 encloses the open end of the extension segment 46 of the solution transporting tube 45. The collar shoulder 53 of the body 51 serves to guide the stopping element 50 at the time when the stopping element 50 is caused to descend, so as to ensure that the recessed portion 52 of the stopping element encloses precisely the open end of the extension segment 46 of the solution transporting tube 45. A compartment 55 is formed between the inner wall of the stopping element 50 and the outer wall of the extension segment 46, as shown in FIG. 6. The compartment 55 has two open ends lower in level than the open end of the extension segment 46 of the solution transporting tube 45. As a result, the level of the solution in the solution dispensing device 41 is lower than the level of the open end of the extension segment 46. However, the compartment 55 contains the solution, which works to shut off the open ends of the compartment 55, thereby preventing the air from getting to the open end of the extension segment 46 of the solution transporting tube 45.

Figure 7:
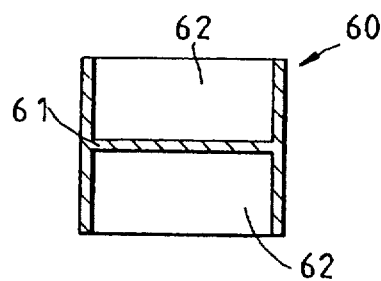
FIG. 7 shows a sectional view of a stopping element of a second preferred embodiment of the present invention.
Figure 8:
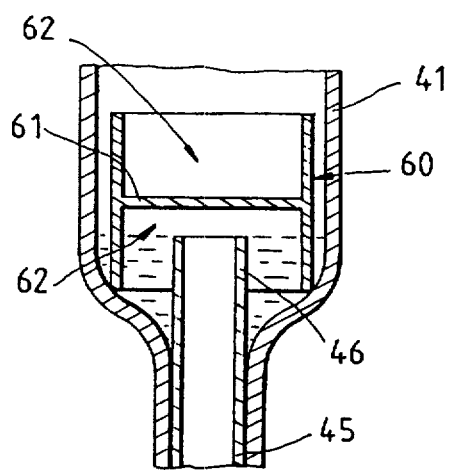
FIG. 8 is a schematic view showing the automatic shut-off of the second preferred embodiment of the present invention.

As shown in FIGS. 7 and 8, a stopping element 60 of the second preferred embodiment of the present invention has a body 61 provided with two recessed portions 62 such that the body 61 has an H-shaped longitudinal section. The stopping element 60 of tubular construction is provided centrally with a partition separating the two recessed portions 62 which have specific functions.

Figure 9:
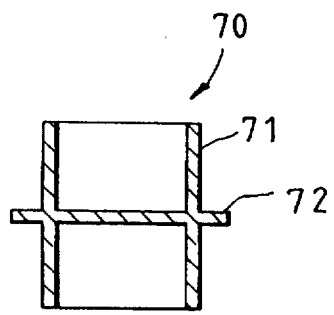
FIG. 9 shows a sectional view of a stopping element of a third preferred embodiment of the present invention.
Figure 10:
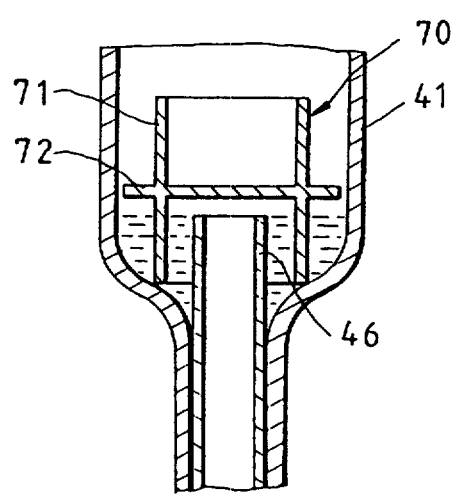
FIG. 10 is a schematic view showing the automatic shut-off of the third preferred embodiment of the present invention.

Now referring to FIGS. 9 and 10, a stopping element 70 of the third preferred embodiment of the present invention is shown to comprise a body 71 having an H-shaped longitudinal section. Located at the midsection of the body 71 is a collar shoulder 72 extending outwardly and horizontally in such a manner that the collar shoulder 72 does not make contact with the inner wall of the solution dispensing device 41. Both upper and lower portions of the stopping element 70 have specific functions.

Figure 11:
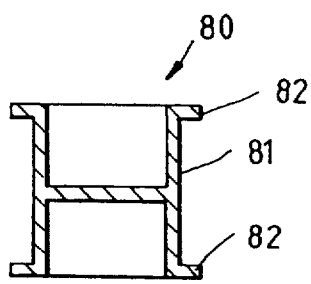
FIG. 11 shows a sectional view of a stopping element of a fourth preferred embodiment of the present invention.
Figure 12:
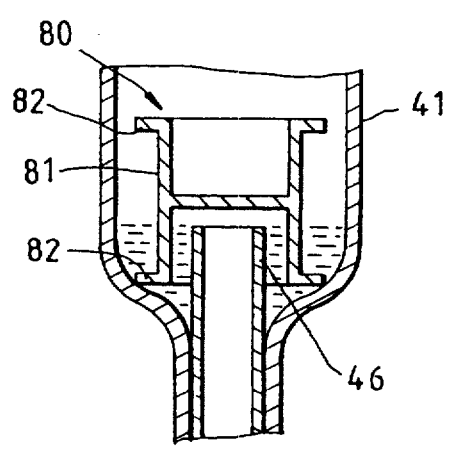
FIG. 12 shows a schematic view illustrating the automatic shut-off of the fourth preferred embodiment of the present invention.

A stopping element 80 of the fourth preferred embodiment of the present invention is shown in FIGS. 11 and 12 and is composed of a body 81 having an H-shaped longitudinal section and upper and lower open ends. Each of the upper and the lower open ends of the body 81 is provided with a collar shoulder 82 extending outwardly and horizontally without making contact with the inner wall of the solution dispensing device 41.

It must be noted that the body of the stopping elements embodied in the present invention may be round and tubular in shape or polygonal and tubular in shape. The main purpose of the body of the stopping element of the present invention is to enclose the extension segment 46 of the solution transporting tube 45 in such a way that a compartment is formed for holding therein the solution serving to seal off the open end of the extension segment 46 of the solution transporting tube 45.

What is claimed is:

1. An improved solution dispensing device for intravenous drip comprising:

a container of tubular construction and provided at the top end thereof with a connecting needle piercing through a mouth of a solution bottle, said container being connected at the bottom end thereof with one end of a solution transporting tube having another end that is connected with a hypodermic needle for injecting said solution into the body of a person; and a stopping element disposed in said container such that said stopping element can be suspended in said solution to descend along with the lowering of the level of said solution contained in said container, and that said stopping element shuts off automatically a passageway between said container and said solution transporting tube;

wherein said solution transporting tube extends into the bottom of said container for a predetermined length to form an upright extension segment;

wherein said stopping element is of a cup-shaped construction and disposed in said container such that an opening of said stopping element faces downwards, said stopping element having a height and density permitting said solution to rise to an underside of a top of said stopping element when suspended in said solution, said stopping element capable of descending along with said solution contained in said container so as to cover said extension segment of said solution transporting tube, said underside remaining at a predetermined distance away from said extension segment of said solution transporting tube when a bottom end of said stopping element has reached a lowest position wherein said bottom end presses against an inner bottom wall of said container.

2. The device according to claim 1 wherein said stopping element is provided with a cap-shaped shoulder extending horizontally and outwardly from said opening thereof.

3. The improved solution dispensing device for intravenous drip in accordance with claim 1 wherein said stopping element has a body provided respectively in an upper portion thereof and a lower portion thereof with a recessed portion, said body having an H-shaped longitudinal section.

4. The improved solution dispensing device for intravenous drip in accordance with claim 3 wherein said stopping element has a body provided centrally with a collar shoulder extending outwardly and horizontally without making contact with an inner wall of said container.

5. The improved solution dispensing device for intravenous drip in accordance with claim 3 wherein said stopping element has a body provided with an upper open end and a lower open end, each of said upper open end and said lower open end having respectively a collar shoulder extending outwardly and horizontally without making contact with an inner wall of said container.

* * * * *